(12) United States Patent
Seiki et al.

(10) Patent No.: US 6,875,794 B2
(45) Date of Patent: Apr. 5, 2005

(54) METHOD OF MANUFACTURING METHANOL

(75) Inventors: Yoshio Seiki, Hiroshima-ken (JP);
Tetsuya Imai, Hiroshima-ken (JP);
Kazuto Kobayashi, Hiroshima-ken (JP); Hiroyuki Osora, Hiroshima-ken (JP); Chie Kuwada, Hiroshima-ken (JP); Kazuhiro Morita, Tokyo (JP);
Shuichi Miyamoto, Tokyo (JP)

(73) Assignees: Mitsubish Heavy Industries, Ltd., Tokyo (JP); Mitsubishi Gas Chemical Company, Inc., Tokyo (JP)

( * ) Notice: Subject to any disclaimer, the term of this patent is extended or adjusted under 35 U.S.C. 154(b) by 69 days.

(21) Appl. No.: 10/197,519

(22) Filed: Jul. 18, 2002

(65) Prior Publication Data

US 2003/0092945 A1  May 15, 2003

(30) Foreign Application Priority Data

Jul. 19, 2001  (JP) ...................................... 2001-219932

(51) Int. Cl.$^7$ .............................................. C07C 27/00
(52) U.S. Cl. ...................... 518/705; 518/700; 518/704
(58) Field of Search .............................. 518/700, 704, 518/705

(56) References Cited

U.S. PATENT DOCUMENTS 4,581,128 A  *  4/1986  Plummer et al. ....... 208/208 R 6,218,439 B1  4/2001  Kobayashi et al.

FOREIGN PATENT DOCUMENTS

| EP | 0 650 950 | 5/1995 |
|----|-----------|--------|
| EP | 1 008 577 | 6/2000 |
| EP | 1 182 185 | 2/2002 |
| GB | 2 213 817 | 8/1989 |
| JP | 1-180841  | 7/1989 |

* cited by examiner

Primary Examiner—J. Parsa
(74) Attorney, Agent, or Firm—Oblon, Spivak, McClelland, Maier & Neustadt, P.C.

(57) ABSTRACT

A method of manufacturing methanol comprising producing a synthesis gas containing hydrogen, carbon monoxide and carbon dioxide, allowing reaction of the synthesis gas to take place over a catalyst to produce a crude methanol, separating the crude methanol into unreacted gas and liquid crude methanol, and distilling the liquid crude methanol to separate it into refined methanol and waste water. Carbon dioxide in combustion exhaust gas to be discharged from a reformer is recovered, and that in feeding the carbon dioxide to the upstream side and/or the downstream side of the reformer, part of the unreacted gas is utilized as a purge gas, a portion of which being utilized as a fuel for a combustion device of the reformer, while the balance of the purge gas being utilized as a fuel for other heating sources and/or as an agent for desulfurizing raw gas.

12 Claims, 4 Drawing Sheets

METHOD OF MANUFACTURING METHANOL

CROSS-REFERENCE TO RELATED APPLICATIONS

This application is based upon and claims the benefit of priority from the prior Japanese Patent Application No. 2001-219932, filed Jul. 19, 2001, the entire contents of which are incorporated herein by reference.

BACKGROUND OF THE INVENTION

1. Field of the Invention

This invention relates to a method of manufacturing methanol.

2. Description of the Related Art

Jpn. Pat. Appln. KOKAI Publication No. 1-180841 discloses a method of manufacturing methanol ($CH_2OH$) from hydrocarbon such as natural gas. Specifically, this publication describes a method of manufacturing methanol, which comprises:

reacting a gaseous hydrocarbon or a vaporized liquid hydrocarbon, by making use of a reformer, with water vapor in the presence of a nickel catalyst at a temperature ranging from 800 to 1000° C. to produce a synthesis gas comprising, as main components, hydrogen ($H_2$), carbon monoxide (CO) and carbon dioxide ($CO_2$);

allowing reaction of the synthesis gas to take place over a copper-based methanol-synthesizing catalyst which is placed inside a synthesis reactor at a pressure of 50 to 150 atm and at a temperature of 200 to 300° C. to produce crude methanol;

cooling the crude methanol;

separating the cooled crude methanol into unreacted gas and liquid crude methanol; and distilling the liquid crude methanol in one or more distillation columns to separate refined methanol and a waste water containing organic compounds having a lower boiling point than that of methanol (hereinafter, referred to as low boiling point organic compounds), another organic compounds having a higher boiling point than that of organic acid and methanol (hereinafter, referred to as high boiling point organic compounds).

In the aforementioned synthesis gas-producing step, by making use of a carbon dioxide recovery apparatus, carbon dioxide is recovered from a combustion exhaust gas which has been discharged from the reformer, and the carbon dioxide thus recovered is fed to the upstream side of the reformer and/or the downstream side of the reformer to obtain a synthesis gas having a desired molar ratio of $H_2/(CO+CO_2)$ which is suitable for the manufacture of methanol.

Further, in synthesizing the crude methanol, the crude methanol is separated into liquid crude methanol and unreacted gas containing rich hydrogen by making use of a gas-liquid separator. A predetermined portion of this unreacted gas is recycled to the upstream side of the synthesizing reactor, while a redundant portion of this unreacted gas is entirely returned to the combustion device of the reformer to enable this redundant portion of unreacted gas to be utilized as part of fuel.

According to the conventional method of manufacturing methanol, hydrogen-rich purge gas is entirely utilized as a fuel for the reformer. However, when all of the hydrogen-rich purge gas is combusted as a fuel for the reformer, the quantity of water vapor in the combustion exhaust gas to be generated in the combustion device of the reformer is increased as compared with the case where a natural gas containing hydrocarbons as main components is combusted as a fuel in the reformer. If a combustion exhaust gas containing such a large quantity of water vapor is to be cooled by introducing it into the cooling column of the carbon dioxide-recovering device, a large quantity of cooling heat quantity is required.

BRIEF SUMMARY OF THE INVENTION

An object of the present invention is to provide a method of manufacturing methanol, which is capable of reducing the cooling heat quantity on the occasion of recovering carbon dioxide without inviting an increase in quantity of fuel to be consumed in a methanol manufacturing plant.

According to the present invention, there is provided a method of manufacturing methanol comprising: reacting hydrocarbons with water vapor in a reformer to produce a synthesis gas containing hydrogen, carbon monoxide and carbon dioxide; allowing reaction of the synthesis gas to take place over a methanol-synthesizing catalyst to produce a crude methanol; cooling the crude methanol; separating the cooled crude methanol into unreacted gas and liquid crude methanol; and distilling the liquid crude methanol to separate it into refined methanol and waste water containing low boiling point organic compounds and high boiling point organic compounds;

wherein carbon dioxide in combustion exhaust gas to be discharged from the reformer is recovered in a carbon dioxide recovering apparatus, and that in feeding the carbon dioxide thus recovered to the upstream side and/or the downstream side of the reformer, part of the unreacted gas is utilized as a purge gas, a portion of which being utilized as a fuel for a combustion device of the reformer, while the balance of the purge gas being utilized as a fuel for other heating sources and/or as an agent for desulfurizating raw gas.

According to the present invention, there is further provided a method of manufacturing methanol comprising: reacting hydrocarbons with water vapor in a reformer to produce a synthesis gas containing hydrogen, carbon monoxide and carbon dioxide; allowing reaction of the synthesis gas to take place over a methanol-synthesizing catalyst to produce a crude methanol; cooling the crude methanol; separating the cooled crude methanol into unreacted gas and liquid crude methanol; and distilling the liquid crude methanol to separate it into refined methanol and waste water containing low boiling point organic compounds and high boiling point organic compounds;

wherein carbon dioxide in combustion exhaust gas to be discharged from the reformer is recovered in a carbon dioxide recovery apparatus, and that in feeding the carbon dioxide thus recovered to the upstream side and/or the downstream side of the reformer, part of the unreacted gas is used as a purge gas for enabling it to be utilized as a fuel for heating sources except for a combustion device of the reformer and/or as an agent for desulfurizating raw gas.

In the method of manufacturing methanol according to the present invention, at least one of the other heating sources may be a boiler.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in, and constitute a part of, the specification, illustrate presently preferred embodiments of the invention, and together with the general description given above, and the detailed description of the preferred embodiments given below, serve to explain the principles of the invention.

DETAILED DESCRIPTION OF THE INVENTION

Next, the methods of manufacturing methanol according to the present invention will be explained with reference to drawings.
(First Embodiment)

Figure 1:
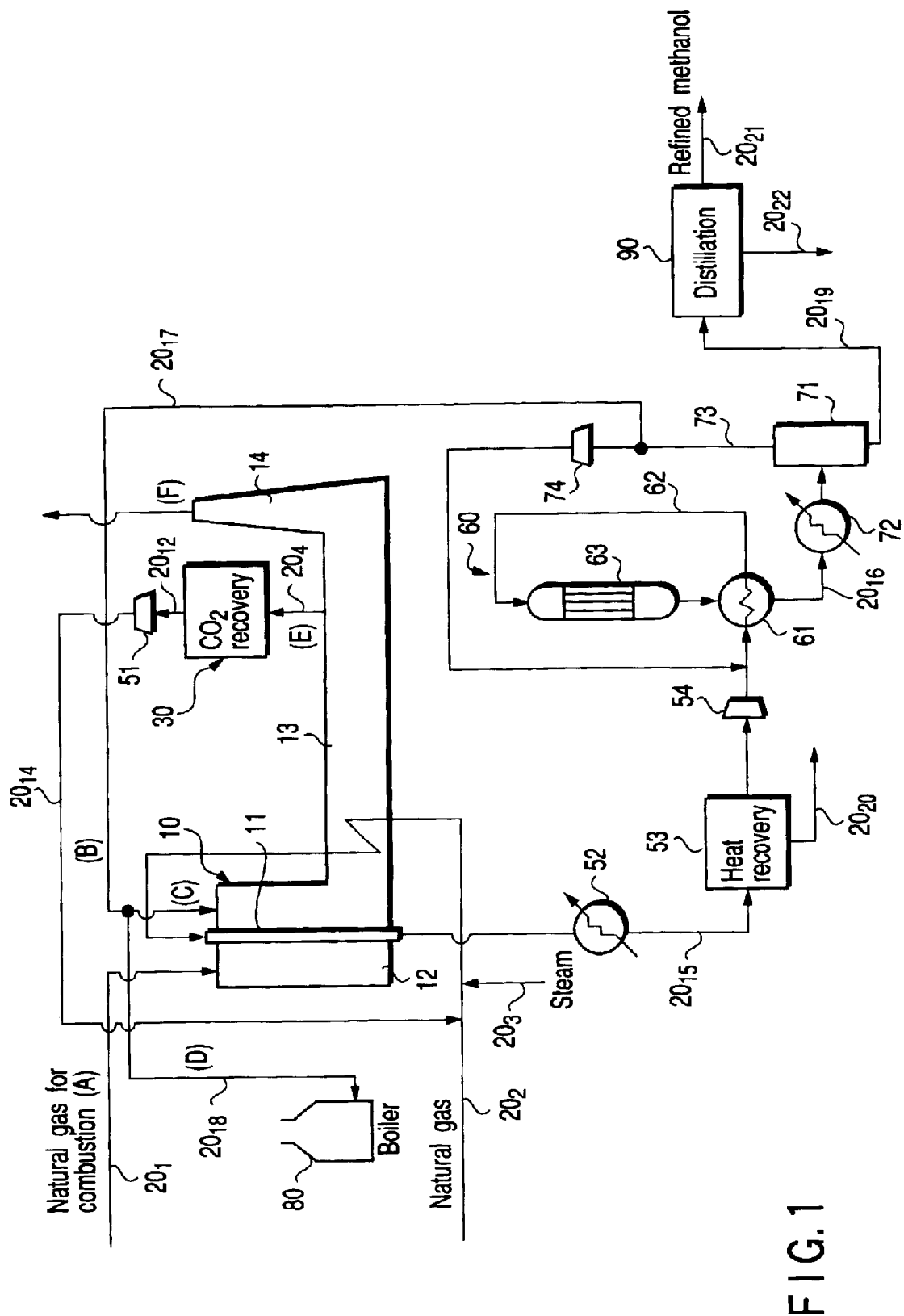
FIG. 1 is a flow chart schematically illustrating one example of the plant for manufacturing methanol according to a first embodiment of the present invention.
Figure 2:
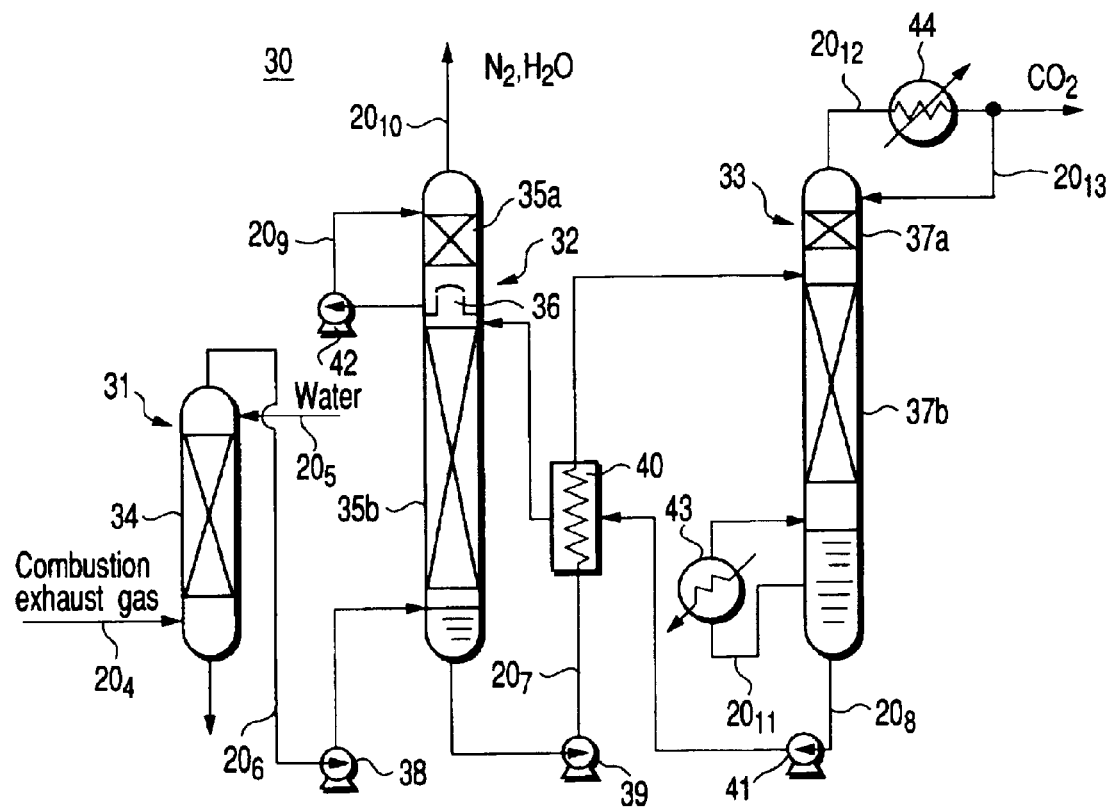
FIG. 2 is a flow chart schematically illustrating the carbon dioxide recovery apparatus shown in FIG. 1.

FIG. 1 schematically illustrates a methanol manufacturing plant to be employed in the manufacture of methanol according to a first embodiment of the present invention; and FIG. 2 schematically illustrates the carbon dioxide recovery apparatus shown in FIG. 1 wherein a carbon dioxide-absorbing liquid is employed.

A reformer 10 is provided with a steam-reforming reaction tube 11, a combustion device 12 for combusting fuel for heating the reaction tube 11, and a chimney 14 communicated via a convection portion (exhaust heat recovery portion) 13 with the combustion device 12. The reaction tube 11 is filled with a nickel-based catalyst for instance. A fuel feeding passageway $20_1$ is connected with the combustion device 12 of the reformer 10.

A raw gas-feeding passageway $20_2$ is connected through the convention portion 13 of the reformer 10 with the top end of the reaction tube 11. A water vapor-feeding passageway $20_3$ is connected with the raw gas-feeding passageway $20_2$ which is located on the upstream side of the convention portion 13.

By the way, the raw gas-feeding passageway $20_2$ may be provided with a desulfurizing device (not shown). Alternatively, the passageway $20_{17}$ to be discussed hereinafter may be branched so as to connect it with the raw gas-feeding passageway $20_2$ to permit part of hydrogen-rich purge gas being supplied from the passageway $20_{17}$ to mix with raw natural gas flowing through the raw gas-feeding passageway $20_2$, thereby enabling the sulfur content in the raw natural gas to turn into the form of hydrogen sulfide which is subsequently adsorbed and removed by the desulfurization device.

A carbon dioxide recovery apparatus 30 is connected through a combustion exhaust gas-feeding passageway $20_4$ with the convection portion 13 of the reformer 10. This carbon dioxide recovery apparatus 30 is provided with a cooling column 31, a carbon dioxide absorption tower 32 and an absorbing liquid regenerating tower 33, all of which are arranged neighboring each other as shown in FIG. 2. The cooling column 31 is provided therein with a gas-liquid contacting member 34. The carbon dioxide absorption tower 32 is provided therein with a couple of upper and lower gas-liquid contacting members 35a and 35b, between which an overflow portion 36 for a regenerated absorbing liquid is disposed. The absorbing liquid regenerating tower 33 is provided therein with a couple of upper and lower gas-liquid contacting members 37a and 37b.

The cooling column 31 is connected via the combustion exhaust gas-feeding passageway $20_4$ with the convection portion 13. It is designed such that the cooling water can be sprayed onto an upper portion of the cooling tower 31 through a passageway $20_5$, and that the combustion exhaust gas that has been introduced through the passageway $20_5$ into the cooling tower 31 is cooled by the gas-liquid contacting member 34. The top portion of the cooling tower 31 is connected via a passageway $20_6$ with a lower portion of the carbon dioxide absorption tower 32, and this passageway $20_6$ is provided with a blower 38. The bottom of the carbon dioxide absorption tower 32 is connected through a passageway $20_7$ with an upper portion of the absorbing liquid regenerating tower 33 which is located between the upper and lower gas-liquid contacting members 37a and 37b. A pump 39 and a heat exchanger 40 are successively mounted on the passageway $20_7$, the pump 39 being located closer to the carbon dioxide absorption tower 32 than the heat exchanger 40. The bottom of the absorbing liquid regenerating tower 33 is connected through a passageway $20_8$ with an upper portion of the carbon dioxide absorption tower 32 where an overflow portion 36 is located, the passageway $20_8$ being provided so as to pass through a heat exchanger 40. A pump 41 is mounted on a region of the passageway $20_8$ which is located between the bottom of the absorbing liquid regenerating tower 33 and the heat exchanger 40.

A passageway $20_9$ is communicated with the carbon dioxide absorption tower 32 in such a way that one end thereof is connected with the overflow portion 36 of the carbon dioxide absorption tower 32 and the other end thereof is connected via a pump 42 with a portion of the carbon dioxide absorption tower 32 which is located over the upper gas-liquid contacting member 35a. An exhaust passageway $20_{10}$ is connected with a top portion of the carbon dioxide absorption tower 32. A passageway $20_{11}$ is communicated with the absorbing liquid regenerating tower 33 in such a way that one end thereof is connected with a lower portion of the absorbing liquid regenerating tower 33 and the other end thereof is connected via a heat exchanger 43 for executing heat exchange with steam with a portion of the absorbing liquid regenerating tower 33 which is located immediately below the lower gas-liquid contacting member 37b. Further, a passageway $20_{12}$ is provided in such a manner that one end thereof is connected with a top portion of the absorbing liquid regenerating tower 33 and the other end thereof is connected, via a cooling heat exchanger 44, with a compressor to be explained hereinafter. From a region of the passageway $20_{12}$ which is located on the downstream side of this cooling heat exchanger 44, another passageway $20_{13}$ is branched so as to be connected with a portion of the absorbing liquid regenerating tower 33 which is located immediately over the upper gas-liquid contacting member 37a.

The carbon dioxide recovery apparatus 30 is connected through the passageway $20_{12}$ with a compressor 51, which is connected via a passageway $20_{14}$ with the raw gas-feeding passageway $20_2$ which is provided on the upstream side of the reformer 10.

The reaction tube 11 of the reformer 10 is connected through a passageway $20_{15}$ with a methanol-synthesizing reaction apparatus 60, the passageway $20_{15}$ being provided with a heat exchanger 52, a heat recovery device 53 and a compressor 54. This reaction apparatus 60 is provided not only with a preheater 61, but also with a methanol synthesizing reactor 63 to which a synthesizing gas is fed via a circulating passageway 62 from the preheater 61. This methanol synthesizing reactor 63 is filled with a methanol-synthesizing catalyst.

The reactor 63 of the reaction apparatus 60 is connected, via the preheater 61 and through a passageway $20_{16}$, with a gas-liquid separator 71. This passageway $20_{16}$ is provided with a cooling heat exchanger 72. The gas-liquid separator 71 is connected through a gas circulating passageway 73 with a region of the passageway $20_{15}$ which is located close to the inlet of the preheater 61. The gas circulating passageway 73 is provided with a gas compressor 74. A purge gas passageway $20_{17}$ is branched from a portion of the gas circulating passageway 73 which is located between the gas-liquid separator 71 and the gas compressor 74, and is connected with the combustion device 12 of the reformer 10. Further, an intermediate portion of the purge gas passageway $20_{17}$ is branched forming a branched purge gas passageway $20_{18}$ with which a boiler 80 is connected.

The gas-liquid separator 71 is connected through a passageway $20_{19}$ with a distillation apparatus 90.

Next, a method of manufacturing methanol will be explained with reference to the methanol manufacturing plant shown in FIGS. 1 and 2.

1) Synthesis Gas Producing Step

First of all, a fuel for combustion, e.g. natural gas is fed through the fuel feeding passageway $20_1$ to the combustion device 12 of the reformer 10. A portion of unreacted gas mainly containing hydrogen which is generated from the gas-liquid separator 71 is utilized as a purge gas and fed through the purge gas passageway $20_{17}$ to the combustion device 12 of the reformer 10. In this combustion device 12, the aforementioned natural gas and purge gas are allowed to combust together with air to heat the interior of the reaction tube 11 up to a sufficiently high temperature, for example, 850 to 900° C. The reason for heating the reaction tube 11 to such a high temperature is due to the fact that the reforming reaction inside the reformer 10 is an endothermic reaction. The combustion exhaust gas containing carbon dioxide that has been generated in the combustion device 12 is transferred through the convection portion 13 to the chimney 14. this combustion exhaust gas is cooled, as it passes through the convection portion 13, by the heat exchange thereof with the natural gas passing through the raw gas-feeding passageway $20_2$ and being mixed with steam as well as by the heat exchange thereof with boiler water (not shown).

The combustion exhaust gas cooled in this manner is fed through the combustion exhaust gas-feeding passageway $20_4$ to the cooling tower 31 of the carbon dioxide recovery apparatus 30 shown in FIG. 2, and is further cooled at the gas-liquid contacting member 34 by cooling water which is fed through the passageway $20_5$. The combustion exhaust gas thus cooled is fed through the passageway $20_6$ to a lower portion of the carbon dioxide absorption tower 32 from a top portion of the cooling tower 31 by the actuation of the blower 38. During the period this combustion exhaust gas is being moved upward through the lower gas-liquid contacting member 35b disposed inside the carbon dioxide absorption tower 32, the carbon dioxide included in the combustion exhaust gas is permitted to contact with a regenerating absorbing liquid, e.g. a regenerating amine solution, that has been fed from the absorbing liquid regenerating tower 33 through the passageway $20_8$ (which passes through the heat exchanger 40) to the overflow portion 36 of the carbon dioxide absorption tower 32, thereby enabling the carbon dioxide to be absorbed by the amine solution. Further, during the period this combustion exhaust gas is being moved upward through the upper gas-liquid contacting member 35a after passing through the overflow portion 36, unreacted carbon dioxide remaining in the combustion exhaust gas is permitted to contact with a regenerating amine solution that has been fed through the passageway $20_9$ to a top portion of the carbon dioxide absorption tower 32 by the actuation of the pump 42, thereby enabling the unreacted carbon dioxide to be absorbed by the amine solution. The combustion exhaust gas thus eliminated of carbon dioxide is discharged out of the system through the exhaust passageway $20_{10}$.

The amine solution having carbon dioxide absorbed therein is stored at the bottom portion of the carbon dioxide absorption tower 32. The amine solution thus stored is enabled, by the actuation of the pump 39, to be fed therefrom and via the passageway $20_7$ to an upper portion of the absorbing liquid regenerating tower 33, which is located between a couple of the upper and lower gas-liquid contacting members 37a and 37b of the absorbing liquid regenerating tower 33. In this case, during the period this amine solution having carbon dioxide absorbed therein being passed through the heat exchanger 40 mounted on the passageway $20_7$, the amine solution is heat-exchanged with a regenerated amine solution having a relatively high temperature and passing through the passageway $20_8$ which is connected with the bottom of the absorbing liquid regenerating tower 33, thereby heating up the amine solution and at the same time, cooling the regenerated amine solution passing through the passageway $20_8$ and having a relatively high temperature. The carbon dioxide-absorbed amine solution which has been heated up in this manner is then separated into carbon dioxide and regenerated amine solution during the period the amine solution flows down through the lower gas-liquid contacting member 37b of the heated absorbing liquid regenerating tower 33. This absorbing liquid regenerating tower 33 will be heated by the regenerated amine solution circulating through the passageway $20_{11}$ and heated up by the heat exchanger 43 which is designed to be heat-exchanged with steam for example. The regenerated amine solution which has been heated up in this manner is stored at the bottom of the absorbing liquid regenerating tower 33 and then fed through the passageway $20_8$ to the carbon dioxide absorption tower 32 by the actuation of the pump 41. On the other hand, the carbon dioxide that has been separated from the carbon dioxide-absorbed amine solution is permitted to move up through the upper gas-liquid contacting member 37a and discharged from a top portion of the absorbing liquid regenerating tower 33 and through the passageway $20_{12}$, during which the carbon dioxide is cooled by the cooling heat exchanger 44, thereby enabling the amine vapor being carried together the carbon dioxide to be condensed, the condensed amine solution being subsequently permitted to return via the branched passageway $20_{13}$ to the absorbing liquid regenerating tower 33. The carbon dioxide thus recovered is fed through the passageway $20_{12}$ to the compressor 51.

Natural gas mainly consisted of hydrocarbons such as methane is fed to the raw gas-feeding passageway $20_2$. On this occasion, the carbon dioxide that has been compressed by the compressor 51 is transferred through the passageway $20_{14}$ and added, at a predetermined quantity, to the natural gas existing on the upstream side of the reformer 10 for instance. Further, by way of the water vapor-feeding passageway $20_3$, water vapor (steam) is also added, at a predetermined quantity, to the natural gas which has been mixed with carbon dioxide.

By the way, it is preferable, on the occasion of mixing carbon dioxide and steam with the natural gas, to set the mixing ratio of methane ($CH_4$) in the natural gas: steam ($H_2O$) to 1:1.5–1:5 (based on molar ratio), and the mixing ratio of methane ($CH_4$): carbon dioxide ($CO_2$) to 1:0.1–1:3 (based on molar ratio).

The natural gas incorporated with carbon dioxide and steam is permitted to pass through the raw gas-feeding passageway $20_2$ and then, heated during the period the natural gas is permitted to pass through the convection portion 13 of the reformer 10, after which the natural gas is fed to the reaction tube 11 which has been heated up to a sufficient temperature.

All of these steam, carbon dioxide and natural gas consisting mainly of methane ($CH_4$) that have been fed to the reaction tube 11 of the reformer 10 are allowed to react with each other in the presence of a catalyst in the reaction tube 11, wherein the steam-reforming of methane is allowed to take place, thus producing a synthesis gas comprising hydrogen, carbon monoxide and carbon dioxide according to the following formulas (1) and (2).

$$CH_4 + H_2O \rightleftharpoons CO + 3H_2 \qquad (1)$$

$$CO + H_2O \rightleftharpoons CO_2 + H_2 \qquad (2)$$

As seen from these formulas (1) and (2) of reforming reaction, as a result of the reaction between one mole of methane and two moles of steam, four moles of hydrogen and one mole of carbon dioxide are produced. In the actual reaction system however, a composition which is close to the chemical reaction equilibrium composition that will be determined by the outlet temperature and pressure of the reaction tube 11 can be obtained.

2) Crude Methanol Synthesizing Step

The synthesis gas produced in the reformer 10 is fed through the passageway $20_{15}$ to the heat exchanger 52. In this heat exchanger 52, the boiler water is heated by the synthesis gas to generate a steam of high pressure and at the same time, the synthesis gas itself is cooled. This cooled synthesis gas is then fed to the heat recovery device 53 so as to be cooled down to ordinary temperature. At this moment, the steam included in the synthesis gas is turned into condensed water which is passed through the passageway $20_{20}$ so as to be utilized as process water.

The synthesis gas separated from the condensed water is fed through the passageway $20_{15}$ to the compressor 54 so as to be compressed therein to for example, a pressure of 50–150 atm which is suited for the methanol synthesis reaction. The synthesis gas pressurized in this manner is fed through the passageway $20_{15}$ to the preheater 61 of the methanol-synthesizing reaction apparatus 60, in which the synthesis gas is heated up to for example, a temperature of 200–300° C. which is suited for the methanol synthesis reaction. Thereafter, the preheated synthesis gas is fed through the circulating passageway 62 to the methanol synthesizing reactor 63 which is filled with methanol synthesis catalyst. By the way, the unreacted gas which has been separated at the gas-liquid separator 71, to be explained hereinafter, is fed through the gas circulating passageway 73 to a region of the passageway $20_{15}$ which is located immediately before the preheater 61, thereby enabling the unreacted gas to be mixed with the synthesis gas. In the methanol synthesizing reactor 63, a product containing methanol that has been synthesized according to the reactions as shown in the following formulas (3) and (4) can be obtained.

$$CO + 2H_2 \rightleftharpoons CH_3OH \qquad (3)$$

$$CO_2 + 3H_2 \rightleftharpoons CH_3OH + H_2O \qquad (4)$$

Furthermore, due to side reactions, impurities such as dimethyl ether and ethanol are produced. These impurities and water are permitted to be included in a liquid crude methanol together with methanol included in the aforementioned product.

3) Liquid Crude Methanol Recovering Step

The product obtained from the methanol synthesizing reactor 63 is successively fed through the circulating passageway 62 and the passageway $20_{16}$ to the cooling heat exchanger 72 so as to be cooled down to ordinary temperature. At this moment, most of the methanol and steam contained in the product are condensed and permitted to enter as a liquid into the gas-liquid separator 71. In this gas-liquid separator 71, the product is separated into liquid crude methanol and an unreacted gas, i.e., hydrogen-rich unreacted gas mainly consisting of hydrogen.

This hydrogen-rich unreacted gas is then utilized in three states thereof. Namely, in a first utilization state thereof, most of the hydrogen-rich unreacted gas is fed through the gas circulating passageway 73 to the gas compressor 74, in which the hydrogen-rich unreacted gas is compressed and then circulated through the gas circulating passageway 73 to a region of the passageway $20_{15}$ which is located at the inlet of the preheater 61 so as to be fed together with the synthesis gas to the methanol synthesizing reactor 63. In a second utilization state thereof, part of the hydrogen-rich unreacted gas is employed as a purge gas, and a portion of the purge gas is passed through the purge gas passageway $20_{17}$ so as to be utilized as part of the fuel for the combustion device 12 in the reformer 10. In a third utilization state thereof, the balance of the purge gas is allowed to pass through the branched purge gas passageway $20_{18}$ which is branched from the purge gas passageway $20_{17}$ so as to be utilized as a fuel for the boiler 80.

4) Distillation Step

The liquid crude methanol which has been separated by the gas-liquid separator 71 is fed through the passageway $20_{19}$ to the distillation apparatus 90 so as to be separated into refined methanol of high purity and waste water containing by-products, i.e. low boiling point organic compounds and high boiling point organic compounds. The refined methanol is taken out as a product from the passageway $20_{21}$. Whereas, the waste water is discharged out of the system through the passageway $20_{22}$.

Although a predetermined quantity of carbon dioxide was added through the passageway $20_{14}$ to the natural gas existing on the upstream side of the reformer 10 in the above embodiment, a predetermined quantity of carbon dioxide may be added to the natural gas existing on the downstream side of the reformer 10 or to the natural gas existing on both sides, i.e. the upstream and downstream sides of the reformer 10.

As explained above, according to the first embodiment, a portion of the unreacted gas, i.e., hydrogen-rich unreacted gas mainly consisting of hydrogen that has been obtained through the gas-liquid separation of the crude methanol is utilized as a purge gas, and part of this purge gas is utilized as part of the fuel for the combustion device 12 in the reformer 10, and at the same time, the balance of the purge gas is utilized as a fuel for the boiler 80. Therefore, the quantity of steam in the combustion exhaust gas to be generated at the combustion device 12 can be reduced as compared with the case where the entire quantity of the purge gas is fed to the combustion device so as to be utilized as part of the fuel therein. As a result, since the quantity of steam in the combustion exhaust gas can be reduced on the occasion of feeding the combustion exhaust gas to the cooling tower 31 of the carbon dioxide recovery apparatus 30 to cool the combustion exhaust gas down to a temperature which is suited for the absorption thereof by an absorption liquid such as amine solution to be employed in the carbon dioxide absorption tower 32 disposed on the downstream side of the cooling tower 31, the heat quantity for the cooling (for example, the quantity of cooling water to be fed to the cooling tower 31) can be reduced. Therefore, it is now possible to reduce the manufacturing cost of methanol.

Moreover, since the carbon dioxide that has been recovered from the combustion exhaust gas discharged from the combustion device of the reformer (or combustion exhaust gas generated in the boiler) is utilized as the carbon dioxide to be added to the natural gas, the quantity of carbon dioxide to be discharged out of the system in the manufacture of methanol can be reduced. As a result, the economy of methanol manufacturing plant can be improved particularly when the tax to the emission of carbon dioxide is newly introduced or when a more severe regulation for the emission of carbon dioxide is newly enforced.

(Second Embodiment)

Figure 3:
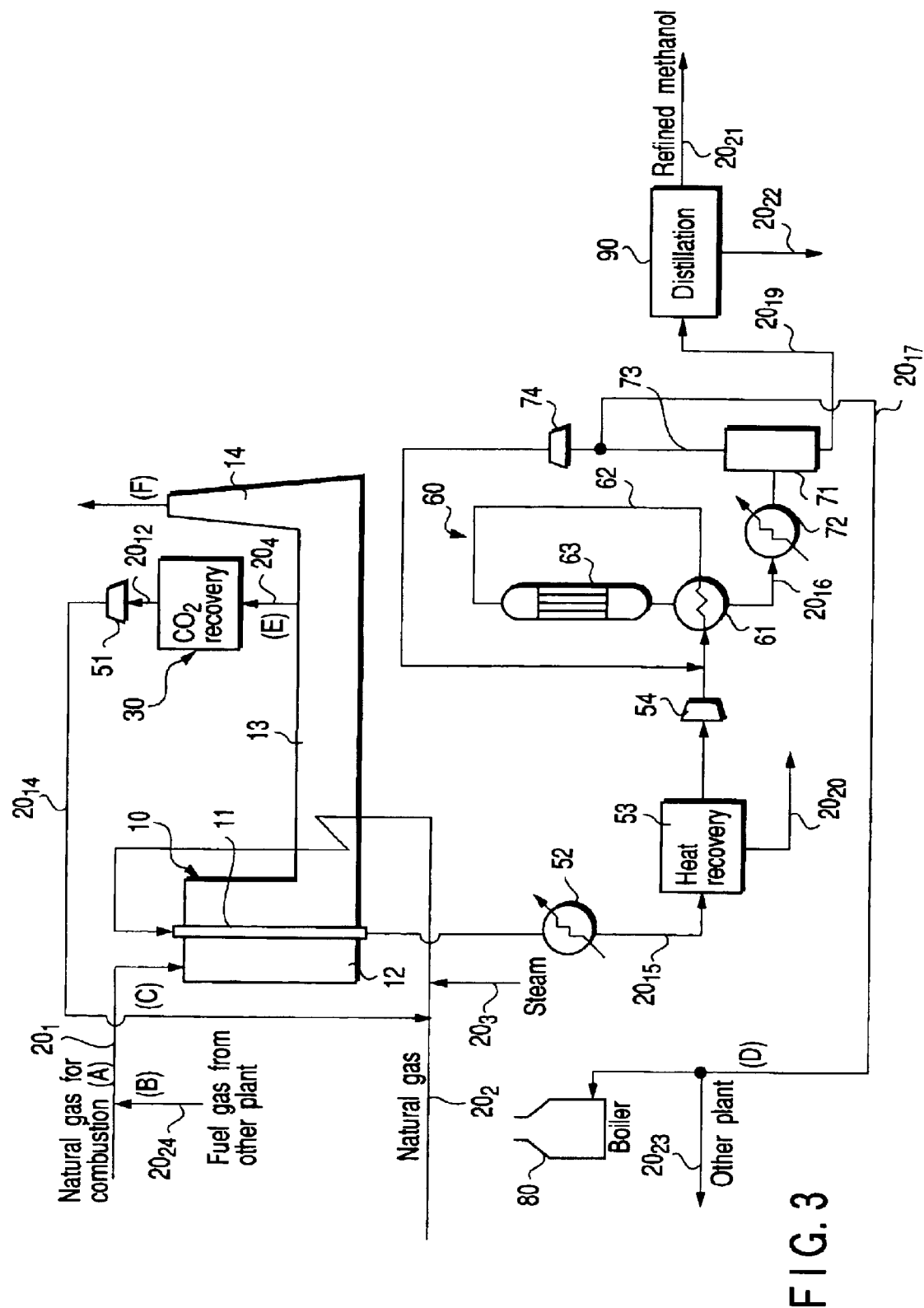
FIG. 3 is a flow chart schematically illustrating one example of the plant for manufacturing methanol according to a second embodiment of the present invention.

FIG. 3 schematically illustrates a methanol manufacturing plant to be employed in the manufacture of methanol according to a second embodiment of the present invention. By the way, the same members or parts as those of FIG. 1 are represented herein by the same reference numerals to thereby omit the explanation thereof.

According to this methanol manufacturing plant, the purge gas passageway $20_{17}$ is branched from the gas-circulating passageway 73 disposed between the gas-liquid separator 71 and the gas compressor 74, and is connected with the boiler 80. Further, the purge gas passageway $20_{17}$ is branched at an intermediate portion thereof, thus forming a branched purge gas passageway $20_{23}$ which is connected with another plant.

According to the plant shown in FIG. 3, methanol is manufactured by substantially the same process as explained above comprising a synthesis gas producing step, a crude methanol synthesizing step, a liquid crude methanol recovery step and a distillation step.

In this methanol manufacturing process, natural gas is fed through the fuel introducing passageway $20_1$ to the combustion device 12 of the reformer 10, and the fuel from another plant is fed from a passageway $20_{24}$, via the fuel introducing passageway $20_1$, to the combustion device 12 of the reformer 10, in which the fuel is combusted together with air to thereby heat the reaction tube 11. Further, a portion of the hydrogen-rich unreacted gas is utilized as a purge gas and passed through the purge gas passageway $20_{17}$ and then, utilized as part of the fuel for the combustion device 12 in the reformer 10. Further, a portion of the hydrogen-rich unreacted gas that has been separated by the gas-liquid separator 71 is fed through the purge gas passageway $20_{17}$ to the boiler 80 so as to be utilized as a fuel for the boiler 80. The balance of the purge gas is allowed to pass through a branched purge gas passageway $20_{23}$ which is branched from the purge gas passageway $20_{17}$ so as to be fed to another plant.

As explained above, according to the second embodiment, a portion of the unreacted gas mainly consisting of hydrogen that has been obtained through the gas-liquid separation of the crude methanol is utilized as a purge gas, and part of this purge gas is utilized as part of the fuel for the boiler 80, and at the same time, the balance of the purge gas is utilized for another plant. Therefore, the quantity of steam in the combustion exhaust gas to be generated at the combustion device 12 can be considerably reduced as compared with the case where the entire quantity of the purge gas is fed to the combustion device so as to be utilized as part of the fuel therein. As a result, since the quantity of steam in the combustion exhaust gas can be reduced on the occasion of feeding the combustion exhaust gas to the cooling tower 31 of the carbon dioxide recovery apparatus 30 as shown in FIG. 2 to cool the combustion exhaust gas down to a temperature which is suited for the absorption thereof by an absorption liquid such as amine solution to be employed in the carbon dioxide absorption tower 32 disposed on the downstream side of the cooling tower 31, the heat quantity for the cooling, for example, the quantity of cooling water to be fed to the cooling tower 31, can be reduced further as compared with the first embodiment. Therefore, it is now possible to further reduce the manufacturing cost of methanol.

By the way, although the way of utilizing the purge gas in the first embodiment differs from that of the second embodiment, the purge gas is utilized as a fuel in both embodiments. Therefore, the total heat balance in these embodiments is the same as the conventional system where the purge gas is entirely utilized in the combustion device of the reformer.

Next, examples of the present invention will be explained in details.

EXAMPLE 1

In this Example 1, the manufacturing method of methanol according to the aforementioned first embodiment will be explained in details with reference to the methanol manufacturing plant shown in FIG. 1.

Fuel such as natural gas and part of the hydrogen-rich purge gas that had been separated by the gas-fuel separator 71 were used as a purge gas, a portion of which was fed to the combustion device 12 of the reformer 10 so as to be combusted together with air in the combustion device 12, while the balance of the purge gas was fed to the boiler 80 so as to be utilized as a fuel for the boiler 80. Further, the natural gas, steam and carbon dioxide which was recovered by means of carbon dioxide recovery apparatus 30 from the combustion exhaust gas delivered from the reformer 10 were fed through the raw gas-introducing passageway $20_2$ to the reaction tube 11 of the reformer 10, in which these raw gases were subjected to steam reforming to obtain a synthesis gas. The synthesis gas thus obtained was treated in the methanol-synthesizing reaction apparatus 60 to produce crude methanol, which was then separated by means of the gas-liquid separator 71 into liquid methanol and a hydrogen-rich unreacted gas. A portion of this hydrogen-rich unreacted gas was returned as the purge gas to the combustion device 12 and also to the boiler 80. Whereas, the liquid crude methanol was fed to the distillation apparatus 90, thereby manufacturing methanol. The composition and flow rate of each of these gases employed in this method of manufacturing methanol are shown in the following Table 1.

By the way, the item (A) in Table 1 represents the natural gas which was fed through the fuel-introducing passageway $20_1$ to the combustion device 12 of the reformer 10, the item (B) represents the total purge gas, the item (C) represents part of the purge gas which was fed to the combustion device 12 of the reformer 10, the item (D) represents the balance of the purge gas which was fed to the boiler 80, the item (E) represents the combustion exhaust gas which was fed from the convection portion 13 to the cooling tower 31 of the carbon dioxide recovery apparatus 30, and the item (F) represents a redundant exhaust gas which was discharged from the chimney 14 of the reformer 10. These items (A) through (F) are also shown in FIG. 1.

EXAMPLE 2

In this Example 2, the manufacturing method of methanol according to the aforementioned second embodiment will be explained in details with reference to the methanol manufacturing plant shown in FIG. 3.

Fuel such as natural gas and part of the hydrogen-rich purge gas that had been separated by the gas-fuel separator 71 were used as a purge gas, a portion of which was fed to the boiler 80 so as to be used as a fuel, while the balance of the purge gas was fed to another plant so as to be utilized as a fuel. Further, the natural gas, steam and carbon dioxide which was recovered by means of carbon dioxide recovery apparatus 30 from the combustion exhaust gas delivered from the reformer 10 were fed through the raw gas-introducing passageway $20_2$ to the reaction tube 11 of the reformer 10, in which these raw gases were subjected to steam reforming to obtain a synthesis gas. The synthesis gas thus obtained was treated in the methanol-synthesizing reaction apparatus 60 to produce crude methanol, which was then separated by means of the gas-liquid separator 71 into liquid methanol and a hydrogen-rich unreacted gas. A portion of this hydrogen-rich unreacted gas was returned as the purge gas to the boiler 80 and also to another plant. Whereas, the liquid crude methanol was fed to the distillation apparatus 90 to thereby manufacture methanol. The composition and flow rate of each of these gases employed in this method of manufacturing methanol are shown in the following Table 2.

By the way, the item (A) in Table 2 represents the natural gas which was fed through the fuel-introducing passageway $20_1$ to the combustion device 12 of the reformer 10, the item (B) represents the fuel introduced from another plant to the fuel-introducing passageway $20_1$, the item (C) represents a total of the natural gas and the fuel which were fed to the combustion device 12 of the reformer 10, the item (D) represents the purge gas which was fed to the boiler 80 and to another plant, the item (E) represents the combustion exhaust gas which was fed from the convection portion 13 to the cooling tower 31 of the carbon dioxide recovery apparatus 30, and the item (F) represents a redundant exhaust gas which was discharged from the chimney 14 of the reformer 10. These items (A) through (F) are also shown in FIG. 3.

COMPARATIVE EXAMPLE 1

Figure 4:
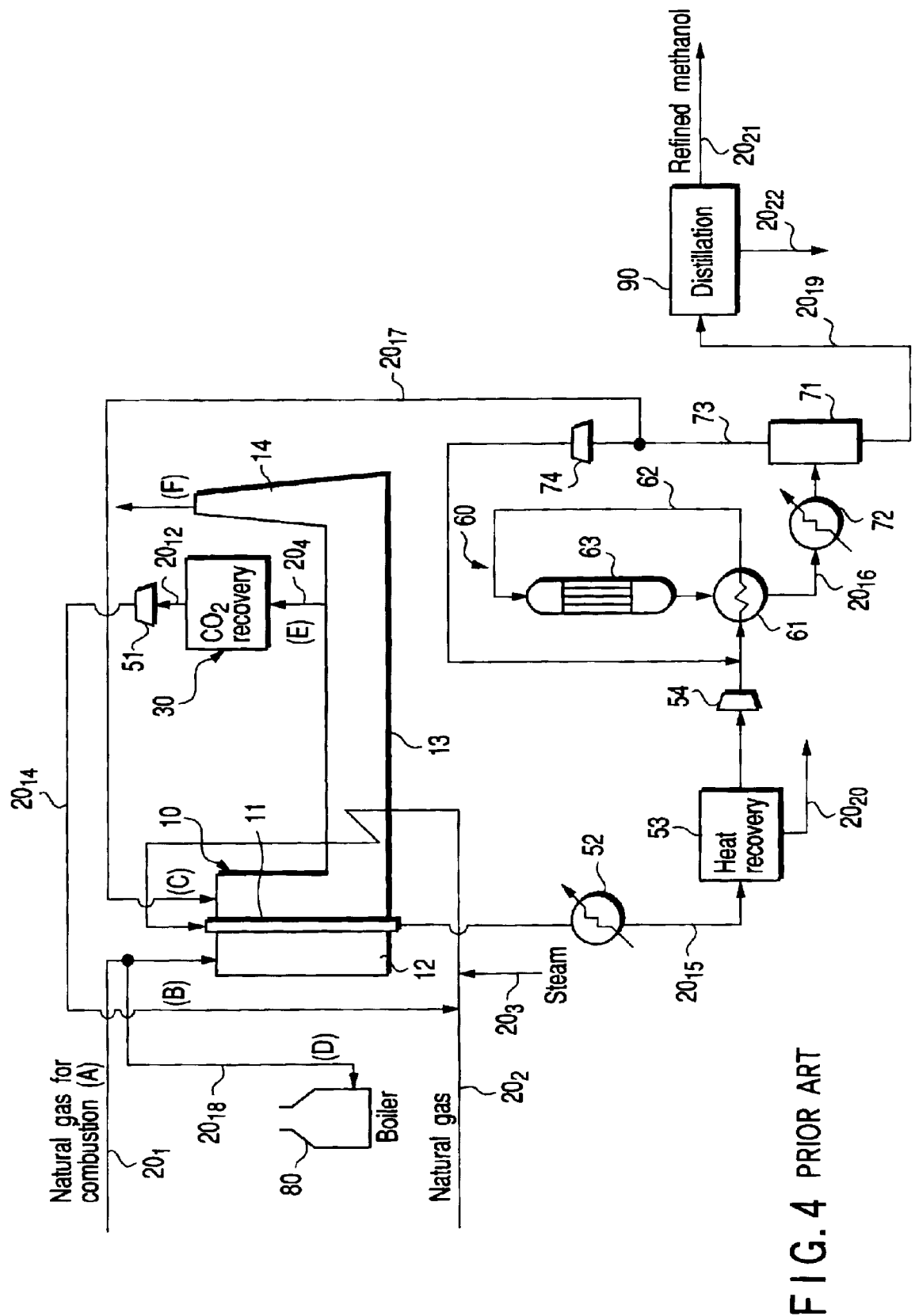
FIG. 4 is a flow chart schematically illustrating one example of the plant for manufacturing methanol according to Comparative Example 1.

FIG. 4 schematically illustrates a methanol-manufacturing plant to be employed for manufacturing methanol according to Comparative Example 1.

By the way, the same members or parts as those of FIG. 1 are represented herein by the same reference numerals to thereby omit the explanation thereof. By making use of this methanol-manufacturing plant, fuel such as natural gas and part of the hydrogen-rich purge gas that had been separated by the gas-fuel separator 71 were used as a purge gas, all of which was fed to the combustion device 12 of the reformer 10 so as to be combusted together with air in the combustion device 12. Further, the natural gas, steam and carbon dioxide which was recovered by means of carbon dioxide recovery apparatus 30 from the combustion exhaust gas delivered from the reformer 10 were fed through the raw gas-introducing passageway $20_2$ to the reaction tube 11 of the reformer 10, in which these raw gases were subjected to steam reforming to obtain a synthesis gas. The synthesis gas thus obtained was treated in the methanol-synthesizing reaction apparatus 60 to produce crude methanol, which was then separated by means of the gas-liquid separator 71 into liquid methanol and a hydrogen-rich unreacted gas. Part of this hydrogen-rich unreacted gas was entirely returned as the purge gas to the combustion device 12. Whereas, the liquid crude methanol was fed to the distillation apparatus 90 to thereby manufacture methanol. The composition and flow rate of each of these gases employed in this method of manufacturing methanol are shown in the following Table 3.

By the way, the item (A) in Table 3 represents the natural gas which was fed to the fuel-introducing passageway $20_1$, the item (B) represents the natural gas which was fed through fuel-introducing passageway $20_1$ to the combustion device 12 of the reformer 10, the item (C) represents a total of the purge gas which was fed to the combustion device 12 of the reformer 10, the item (D) represents the natural gas which was fed through the passageway $20_{18}$ branched from the fuel-introducing passageway $20_1$ to the boiler 80, the item (E) represents the combustion exhaust gas which was fed from the convection portion 13 to the cooling tower of the carbon dioxide recovery apparatus 30, and the item (F) represents a redundant exhaust gas which was discharged from the chimney 14 of the reformer 10. These items (A) through (F) are also shown in FIG. 4.

The ratio of cooling heat quantity per 1000 kg of carbon dioxide ($CO_2$) that had been recovered in the manufacture of methanol in each of Examples 1 and 2 and Comparative Example 1 is shown in the following Table 4.

TABLE 1

(Example 1)

| | (A) | (B) | (C) | (D) | (E) | (F) |
|---|---|---|---|---|---|---|
| $CH_4$ [$m^3N/h$] | 11000 | 10300 | 9600 | 700 | 0 | 0 |
| $C_nH_{2n+2}$ | 790 | 0 | 0 | 0 | 0 | 0 |
| CO | 0 | 670 | 630 | 40 | 0 | 0 |
| $CO_2$ | 0 | 1300 | 1200 | 100 | 18000 | 6700 |
| $H_2$ | 0 | 76700 | 71900 | 4800 | 0 | 0 |
| $N_2$ | 100 | 660 | 620 | 40 | 253900 | 94100 |
| $CH_3OH$ | 0 | 490 | 460 | 30 | 0 | 0 |
| $H_2O$ | 0 | 40 | 30 | 10 | 101900 | 37800 |
| TOTAL | 11890 | 90160 | 84440 | 5720 | 373800 | 138600 |

TABLE 2

(Example 2)

| | (A) | (B) | (C) | (D) | (E) | (F) |
|---|---|---|---|---|---|---|
| $CH_4$ [$m^3N/h$] | 11000 | 28200 | 39200 | 10300 | 0 | 0 |
| $C_nH_{2n+2}$ | 790 | 2010 | 2800 | 0 | 0 | 0 |
| CO | 0 | 0 | 0 | 670 | 0 | 0 |
| $CO_2$ | 0 | 0 | 0 | 1300 | 18000 | 26900 |
| $H_2$ | 0 | 0 | 0 | 76700 | 0 | 0 |
| $N_2$ | 100 | 240 | 340 | 660 | 150700 | 225900 |

TABLE 2-continued (Example 2)

|  | (A) | (B) | (C) | (D) | (E) | (F) |
|---|---|---|---|---|---|---|
| $CH_3OH$ | 0 | 0 | 0 | 490 | 0 | 0 |
| $H_2O$ | 0 | 0 | 0 | 40 | 44800 | 67100 |
| TOTAL | 11890 | 30450 | 42340 | 90160 | 213500 | 319900 |

TABLE 3

(Comparative Example 1)

|  |  | (A) | (B) | (C) | (D) | (E) | (F) |
|---|---|---|---|---|---|---|---|
| $CH_4$ | [$m^3N/h$] | 11000 | 9100 | 10300 | 1900 | 0 | 0 |
| $C_nH_{2n+2}$ |  | 790 | 650 | 0 | 140 | 0 | 0 |
| CO |  | 0 | 0 | 670 | 0 | 0 | 0 |
| $CO_2$ |  | 0 | 0 | 1300 | 0 | 18000 | 5300 |
| $H_2$ |  | 0 | 0 | 76700 | 0 | 0 | 0 |
| $N_2$ |  | 100 | 80 | 660 | 20 | 267200 | 78900 |
| $CH_3OH$ |  | 0 | 0 | 490 | 0 | 0 | 0 |
| $H_2O$ |  | 0 | 0 | 40 | 0 | 109300 | 32300 |
| TOTAL |  | 11890 | 9830 | 90160 | 2060 | 394500 | 116500 |

TABLE 4

|  | Efficiency of cooling tower (Gcal/h) | Cooling heat quantity per 1000 kg of $CO_2$ recovered (Gcal/1000 kg-$CO_2$) | Ratio of cooling heat quantity |
|---|---|---|---|
| Comparative Example 1 | 54 | 1.80 | 100 |
| Example 1 | 51 | 1.68 | 93 |
| Example 2 | 22 | 0.73 | 41 |

As clearly seen from Tables 1 to 4, the quantity of steam in the combustion exhaust gas which was introduced into the carbon dioxide recovery apparatus 30 from the convection portion 13 of the reformer 10 in the manufacturing method of methanol according to Example 1 was 101,900 $m^3N/h$, whereas the quantity of steam in the combustion exhaust gas which was introduced into the carbon dioxide recovery apparatus 30 from the convection portion 13 of the reformer 10 in the manufacturing method of methanol according to Comparative Example 1 was as high as 109,300 $m^3N/h$, thus indicating an increase in quantity of steam. It will be seen as shown in Table 4 that it is possible, according to the method of manufacturing methanol of Example 1, to reduce the quantity of cooling heat quantity required for cooling the combustion exhaust gas in the cooling tower of the carbon dioxide recovery apparatus 30 as compared with the method of manufacturing methanol of Comparative Example 1.

Further, the quantity of steam in the combustion exhaust gas which was introduced into the carbon dioxide recovery apparatus 30 from the convection portion 13 of the reformer 10 in the manufacturing method of methanol according to Example 2 was 44,800 $m^3N/h$, which was far smaller than that (101,900 $m^3N/h$) of Example 1, thus making it possible to further reduce the quantity of steam in the combustion exhaust gas. Thus, it will be seen from Table 4 that according to the method of manufacturing methanol of Example 2, the quantity of cooling heat quantity required for cooling the combustion exhaust gas in the cooling tower of the carbon dioxide recovery apparatus 30 can be further reduced as compared with the method of manufacturing methanol of Comparative Example 1.

As explained above, it is possible, according to the present invention, to provide a method of manufacturing methanol, which is capable of reducing the cooling heat quantity on the occasion of recovering carbon dioxide without inviting an increase in heating heat quantity, thereby making it possible to reduce the running cost.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing methanol comprising:

reacting hydrocarbons with water vapor in a reformer to produce a synthesis gas comprising hydrogen, carbon monoxide and carbon dioxide; allowing reaction of the synthesis gas to take place over a methanol-synthesizing catalyst to produce a crude methanol; cooling said crude methanol; separating said cooled crude methanol into unreacted gas and liquid crude methanol; and distilling said liquid crude methanol to separate it into refined methanol and waste water comprising low boiling point organic compounds and high boiling point organic compounds; and wherein carbon dioxide in combustion exhaust gas to be discharged from said reformer is recovered in a carbon dioxide-recovering device, and that in feeding the carbon dioxide thus recovered to the upstream side and/or the downstream side of said reformer, a part of said unreacted gas is utilized as a purge gas, a portion of which being utilized as a fuel for a combustion device of said reformer, while the balance of said purge gas being utilized as a fuel for one or more other heating sources, and as an agent for desulfurizing raw gas, and wherein said unreacted gas comprises hydrogen.

2. The method of manufacturing methanol according to claim 1, wherein at least one of said other heating sources is a boiler.

3. A method of manufacturing methanol comprising:

reacting hydrocarbons with water vapor in a reformer to produce a synthesis gas comprising hydrogen, carbon monoxide and carbon dioxide; allowing reaction of the synthesis gas to take place over a methanol-synthesizing catalyst to produce a crude methanol; cooling said crude methanol; separating said cooled crude methanol into unreacted gas and liquid crude methanol; and distilling said liquid crude methanol to separate it into refined methanol and waste water comprising low boiling point organic compounds and high boiling point organic compounds; and wherein carbon dioxide in combustion exhaust gas to be discharged from the reformer is recovered in a carbon dioxide-recovering device, and that in feeding the carbon dioxide thus recovered to the upstream side and/or the downstream side of said reformer, part of said unreacted gas is used as a purge gas for enabling it to be utilized as a fuel for heating sources, except for a combustion device of said reformer, and as an agent for desulfurizing raw gas, and wherein said unreactive gas comprises hydrogen.

4. The method of manufacturing methanol according to claim 3, wherein at least one of said other heating sources is a boiler.

5. The method of manufacturing methanol according to claim 1, wherein said reformer is fueled by a hydrocarbon source.

6. The method of manufacturing methanol according to claim 5, wherein the hydrocarbon source comprises natural gas.

7. The method of manufacturing methanol according to claim 3, wherein said reformer is fueled by a hydrocarbon source.

8. The method of manufacturing methanol according to claim 7, wherein the hydrocarbon source comprises natural gas.

9. The method of manufacturing methanol according to claim 1, further comprising, setting a mixing molar ratio of methane to steam from 1:1.5 to 1:5 in a reaction tube of said reformer.

10. The method of manufacturing methanol according to claim 9, further comprising, setting a mixing molar ratio of methane to carbon dioxide from 1:0.1 to 1:3 in a reaction tube of said reformer.

11. The method of manufacturing methanol according to claim 3, further comprising, setting a mixing molar ratio of methane to steam from 1:1.5 to 1:5 in a reaction tube of said reformer.

12. The method of manufacturing methanol according to claim 11, further comprising, setting a mixing molar ratio of methane to carbon dioxide from 1:0.1 to 1:3 in a reaction tube of said reformer.

* * * * *